United States Patent [19]

Böger et al.

[11] Patent Number: 4,866,079
[45] Date of Patent: Sep. 12, 1989

[54] N-PYRIDYLOXYPHENYLISOTHIOUREAS AND THE USE THEREOF IN PEST CONTROL

[75] Inventors: Manfred Böger, Weil am Rhein, Fed. Rep. of Germany; Jozef Drabek, Oberwil, Switzerland

[73] Assignee: Ciba-Geigy Corporation, Ardsley, N.Y.

[21] Appl. No.: 25,296

[22] Filed: Mar. 12, 1987

[30] Foreign Application Priority Data

Mar. 19, 1986 [CH] Switzerland ............... 1107/86
Feb. 6, 1987 [CH] Switzerland ............... 442/87

[51] Int. Cl.⁴ ............... C07D 213/64; C07D 213/55; A01N 43/40
[52] U.S. Cl. ............... 514/346; 546/300; 546/298
[58] Field of Search ............... 546/298, 300; 514/346

[56] References Cited

U.S. PATENT DOCUMENTS

| | | | |
|---|---|---|---|
| 3,931,201 | 1/1976 | Johnston | 546/291 |
| 4,328,247 | 5/1982 | Drabek et al. | 514/637 |
| 4,328,248 | 5/1982 | Böger et al. | 514/637 |
| 4,404,225 | 9/1983 | Böger et al. | 514/586 |

OTHER PUBLICATIONS

Japanese Patent No. 58-079979, (Ishihara), Abstract.

*Primary Examiner*—Alan L. Rotman
*Attorney, Agent, or Firm*—Kevin T. Mansfield; Edward McC. Roberts

[57] ABSTRACT

The invention relates to novel N-pyridyloxyphenylisothioureas of formula I

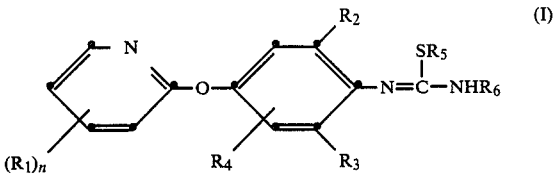

wherein
the substituents $R_1$ are each independently halogen, $C_1$–$C_3$alkyl, a mono- or polyhalogenated $C_1$–$C_3$alkyl group, or —$COOR_7$;
$R_2$, $R_3$ and $R_7$ are each independently $C_1$–$C_5$alkyl, with the proviso that $R_2$ and $R_3$ are not simultaneously methyl if $R_6$ is tert-butyl and the substituents $R_1$ are chlorine and/or trifluoromethyl;
$R_4$ is hydrogen or methyl;
$R_5$ is $C_1$–$C_6$alkyl;
$R_6$ is $C_1$–$C_{12}$alkyl, a mono- or polyhalogenated $C_1$–$C_{12}$alkyl group, $C_1$–$C_6$alkoxy-$C_1$–$C_{12}$alkyl, $C_3$–$C_8$cycloalkyl, a mono- or di($C_1$–$C_3$)alkylated $C_3$–$C_8$cycloalkyl group, $C_3$–$C_8$cycloalkyl-$C_1$–$C_4$-alkyl, or a polycyclic alkyl radical containing 7 to 10 carbon atoms; and
n is 0 to 4;

to their salts with organic or inorganic acids, to the preparation thereof, to their use in pest control, as well as to pesticidal compositions which contain at least one compound of formula I or an active intermediate. The preferred area of application is the control of pests of animals and plants.

19 Claims, No Drawings

N-PYRIDYLOXYPHENYLISOTHIOUREAS AND THE USE THEREOF IN PEST CONTROL

The present invention relates to N-pyridyloxyphenylisothioureas, to their salts with organic or inorganic acids, to the preparation thereof, to pesticidal compositions which contain these compounds or active intermediates, as well as to the use thereof in pest control.

The compounds of this invention are of formula I

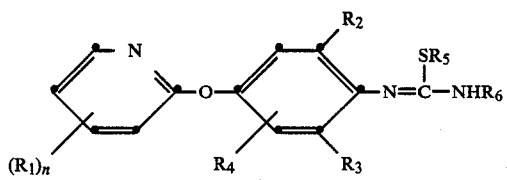

wherein
the substituents $R_1$ are each independently halogen, $C_1$–$C_3$alkyl, a mono- or polyhalogenated $C_1$–$C_3$alkyl group, or —$COOR_7$;
$R_2$, $R_3$ and $R_7$ are each independently $C_1$–$C_5$alkyl, with the proviso that $R_2$ and $R_3$ are not simultaneously methyl if $R_6$ is tert-butyl and the substituents $R_1$ are chlorine and/or trifluoromethyl;
$R_4$ is hydrogen or methyl;
$R_5$ is $C_1$–$C_6$alkyl;
$R_6$ is $C_1$–$C_{12}$alkyl, a mono- or polyhalogenated $C_1$–$C_{12}$alkyl group, $C_1$–$C_6$alkoxy-$C_1$–$C_{12}$alkyl, $C_3$–$C_8$cycloalkyl, a mono- or di($C_1$–$C_3$)alkylated $C_3$–$C_8$cycloalkyl group, $C_3$–$C_8$cycloalkyl-$C_1$–$C_4$-alkyl, or a polycyclic alkyl radical containing 7 to 10 carbon atoms; and
n is 0 to 4.

Suitable halogen substituents are fluorine, chlorine, bromine, and iodine, with fluorine and chlorine being preferred.

Alkyl groups suitable as substituents may be straight chain or branched. Examples of such alkyl groups are methyl, ethyl, propyl, isopropyl, butyl, isobutyl, sec-butyl, tert-butyl or pentyl, hexyl, heptyl, octyl and the isomers thereof.

The mono- or polyhalogenated $C_1$–$C_{12}$alkyl groups suitable as substituents may be straight chain or branched and may be only partially halogenated or may be perhalogenated, with halogen in said substituents being as defined above. Particularly suitable examples of such substituents are, inter alia, methyl substituted by 1 to 3 fluorine, chlorine and/or bromine atoms, e.g. $CHF_2$ or $CF_3$; ethyl substituted by 1 to 5 fluorine, chlorine and/or bromine atoms, e.g. $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, each substituted by 1 to 7 fluorine, chlorine and/or bromine atoms, e.g. $CH_2CHBrCH_2Br$, $CF_2CHFCF_3$, $CH_2CF_2CF_3$ or $CH(CF_3)_2$; butyl substituted by 1 to 9 fluorine, chlorine and/or bromine atoms, or an isomer thereof, e.g. $CF(CF_3)CHFCF_3$ or $CH_2(CF_2)_2CF_3$.

The alkoxyalkyl groups suitable as substituents may be straight chain or branched. Examples of such groups are, inter alia, methoxymethyl, methoxyethyl, ethoxyethyl, methoxypropyl, ethoxypropyl, propoxypropyl, methoxybutyl, ethoxybutyl, propoxybutyl or butoxybutyl.

The cyloalkyl groups suitable as substituents are for example cyclopropyl, cyclobutyl, cyclopentyl or cyclohexyl. These groups may be substituted by one or two $C_1$–$C_3$alkyl groups and/or attached through a $C_1$–$C_4$alkylene bridge to the remainder of the molecule.

The polycyclic alkyl radicals suitable as substituents may contain 7 to 10 carbon atoms. Examples of such radicals are, inter alia, bicyclo[2.1.0]heptyl, bicyclo[3.2.1]octyl or bicyclo[3.3.1]nonyl. The compounds of formula I may also be in the form of their acid addition salts. Both organic and inorganic acids are suitable for the formation of such salts. Examples of such acids are, inter alia, hydrochloric acid, hydrobromic acid, nitric acid, various phosphoric acids, sulfuric acid, acetic acid, propionic acid, butyric acid, valeric acid, oxalic acid, malonic acid, maleic acid, fumaric acid, lactic acid, tartaric acid or salicylic acid.

Depending on the value of n, the pyridyl radical may be substituted by several substituents $R_1$. If n is greater than 1, then the various substituents $R_1$ may be identical or different.

Particularly interesting compounds of formula I are those
wherein
the substituents $R_1$ are each independently fluorine, chlorine or a mono- or polyhalogenated $C_1$–$C_3$alkyl group;
$R_2$ and $R_3$ are each independently $C_1$–$C_3$alkyl, with the proviso that $R_2$ and $R_3$ are not simultaneously methyl if $R_6$ is tert-butyl and the substituents $R_1$ are chlorine and/or trifluoromethyl;
$R_4$ is hydrogen;
$R_5$ is $C_1$–$C_3$alkyl;
$R_6$ is $C_1$–$C_8$alkyl, $C_1$–$C_4$alkoxy-$C_1$–$C_4$alkyl, $C_3$–$C_6$cycloalkyl, a mono- or di($C_1$–$C_3$)alkylated $C_3$–$C_6$cycloalkyl group, or $C_3$–$C_6$cycloalkyl-$C_1$–$C_3$alkyl; and
n is 1 or 2.

Preferredcompounds of formula I are those wherein
the substituents $R_1$ are each independently chlorine or $CF_2CFCl_2$;
$R_2$ and $R_3$ are each independently methyl or ethyl, with the proviso that $R_2$ and $R_3$ ae not simultaneously methyl if $R_6$ is tert-butyl and the substituents $R_1$ are chlorine and/or trifluoromethyl;
$R_4$ is hydrogen;
$R_5$ is methyl;
$R_6$ is $C_1$–$C_5$alkyl or $C_3$–$C_6$cycloalkyl; and
n is 2.

Examples of compounds of formula I are, inter alia:

| $R_1$ | $R_2$ | $R_3$ | $R_4$ | $R_5$ | $R_6$ |
| --- | --- | --- | --- | --- | --- |
| 3,5-Cl | $CH_3$ | $CH_3$ | H | $CH_3$ | s-$C_4H_9$ |
| 3,5-Cl | n-$C_3H_7$ | n-$C_3H_7$ | H | $CH_3$ | t-$C_4H_9$ |
| 3,5-Cl | $C_2H_5$ | s-$C_4H_9$ | H | $CH_3$ | t-$C_4H_9$ |
| 3,5-Cl | $CH_3$ | i-$C_5H_{11}$ | H | $CH_3$ | t-$C_4H_9$ |
| 3,5-Cl | $CH_3$ | $CH_3$ | H | $CH_3$ | $CH(i-C_3H_7)_2$ |
| 3,5-Cl | $CH_3$ | $CH_3$ | H | $CH_3$ | $CH(C_2H_5)_2$ |

| R₁ | R₂ | R₃ | R₄ | R₅ | R₆ |
|---|---|---|---|---|---|
| 3,5-Cl | C₂H₅ | C₂H₅ | H | C₂H₅ | t-C₄H₉ |
| 3,5-Cl | C₂H₅ | CH₃ | H | n-C₆H₁₃ | t-C₄H₉ |
| 3,5-Cl | CH₃ | CH₃ | CH₃ | CH₃ | s-C₅H₁₁ |
| 3,5-Cl | CH₃ | CH₃ | C₂H₅ | CH₃ | s-C₄H₉ |
| 3,5-Cl | CH₃ | C₂H₅ | CH₃ | CH₃ | C₄H₉ |
| 4-COOCH₃, 6-Cl | CH₃ | CH₃ | H | CH₃ | t-C₄H₉ |
| 4-COOC₅H₁₁(n), 6-Cl | CH₃ | CH₃ | H | CH₃ | t-C₄H₉ |
| 5-n-C₃H₇ | CH₃ | CH₃ | H | CH₃ | t-C₄H₉ |

The compounds of formula I of the present invention can be prepared by methods which are known per se, for example by reacting a thiourea of formula II

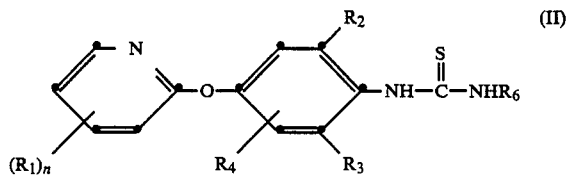

with an alkylating agent of formula III $$R_5-X \quad \text{(III)}$$

in the presence of a base, in which formulae II and III, $R_1$, $R_2$, $R_3$, $R_4$, $R_5$, $R_6$ and n are as defined for formula I and X is a leaving group, e.g. a halogen atom, preferably chlorine, bromine or iodine.

The process is conveniently carried out at a temperature in the range from 0° to 100° C., under normal or slightly increased pressure and preferably in the presence of a solvent or diluent which is inert towards the reactants. Examples of suitable solvents or diluents are ethers or ethereal compounds such as diethyl ether, diisopropyl ether, dioxane or tetrahydrofuran; aromatic hydrocarbons such as benzene, toluene or xylenes; ketones such as acetone, methyl ethyl ketone or cyclohexanone; or alcohols such as methanol or ethanol.

Suitable bases may be of organic or inorganic origin, e.g. sodium hydride, sodium carbonate, calcioum carbonate, tertiary amines such as triethylamine or triethylenediamine, or 4-dimethylaminopyridine or pyridine.

The thioureas of formula II themselves can also be prepared by methods which are known per se, e.g. by reacting an isothiocyanate of formula IV

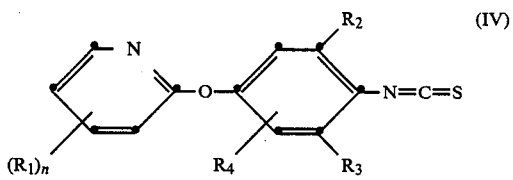

with an amine of formula V $$H_2N-R_6 \quad \text{(V)}$$

in which formulae IV and V $R_1$, $R_2$, $R_3$, $R_4$, $R_6$ and n are as defined for formula I.

The process for the preparation of the compounds of formula II is conveniently carried out in the presence of a solvent or diluent which is inert towards the reactants, at a reaction temperature in the range from 0° to 100° C. and under normal pressure. Suitable solvents or diluents are for example those mentioned above for the process for the preparation of the compounds of formula I. However, it must be noted that alcohols are not suitable solvents in the process for the preparation of the compounds of formula II.

The isothiocyanate of formul IV themselves can be prepared by methods which are known per se, e.g. by reacting a pyridyloxyaniline of formula VI

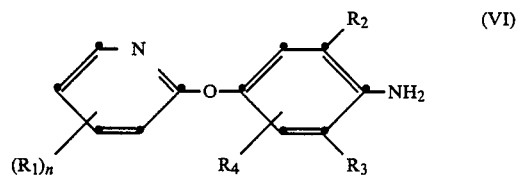

with thiophosgene, in which formula VI $R_1$, $R_2$, $R_3$, $R_4$ and n are as defined for formula I.

The process for the preparation of the compounds of formula IV is conveniently carried out in the presence of an organic or inorganic base, e.g. triethylamine or calcium carbonate, and of a solvent or diluent which is inert towards the reactants, at a temperature in the range from 0° to 100° C. and under normal pressure. Suitable solvents or diluents are, inter alia, those mentioned above for the process for the preparation of the compounds of formula I, or dichloromethane. However, it must be noted that alcohols are not suitable solvents in the process for the preparation of the compounds of formula IV.

The pyridyloxyanilines of formula VI themselves can be prepared by methods which are known per se, e.g. by reacting a hydroxyaniline of formula VII

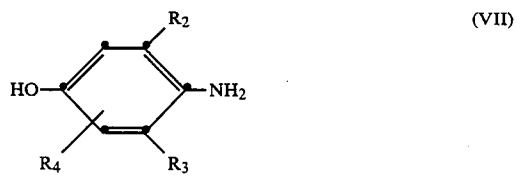

with a halopyridine of formula VIII

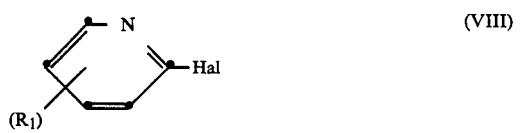

in which formulae VII and VIII $R_1$, $R_2$, $R_3$, $R_4$ and n are as defined for formula I and Hal is a halogen atom, preferably fluorine, chlorine or bromine.

The process for the preparation of the compounds of formula VI is conveniently carried out in the presence of an organic or inorganic base, e.g. an alkali metal hydroxide or carbonate, and of a preferably polar solvent or diluent which is inert towards the reactants, at a temperature in the range from 0° to 100° C. and under normal pressure. Suitable solvents or diluents are those mentioned above for the process for the preparation of the compounds of formula I; dimethyl sulfoxide is also particularly suitable.

The compounds of formulae II, III, IV, V, VI, VII and VIII are either known or they can be prepared by methods which are known per se.

Surprisingly, it has been found that the compounds of formula I of this invention and the intermediates of formula II are valuable pesticides while being well tolerated by warm-blooded animals and plants. The compounds of formulae I and II are therefore suitable e.g. for controlling pests of animals and plants. Such pests belong principally to the phylum of Arthropoda, such as in particular insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera and arachnids of the order Acarina, e.g. mites and ticks. Every development stage of the pests can be controlled, i.e. the adults, pupae and nymphs, and also in particular the larvae and eggs. It is thus possible to control effectively in particular larvae and eggs of phytopathogenic insect pests and mites in crops of ornamentals and useful plants, e.g. in fruit and vegetable crops, and especially in cotton crops. If compounds of formulae I and II are ingested by imagines, then a direct kill of the pests or a reduced oviposition and/or hatching rate can be observed. This last activity can be observed in particular in Coleoptera. In the control of pests that are parasites of animals, in particular of domestic animals and productive livestock, the compounds of the invention are suitable above all against ectoparasites, e.g. mites and ticks and Diptera such as *Lucilia sericata*.

The good pesticidal activity of the compounds of formulae I and II corresponds to a mortality of at least 50–60% of the above pests.

The activity of the compounds of formulae I and II and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and Bacillus thuringiensis preparations.

The compounds of formulae I and II are used in unmodified form, or preferably together with the inert, agriculturally acceptable adjuvants conventionally employed in the art of formulation, and can therefore be formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of application such as spraying, atomising, dusting, scattering or pouring, are chosen in accordance with the intended objectives and the prevailing circumstances.

The formulations, i.e. the compositions, preparations or mixtures containing the compound or compounds (active ingredients) of formulae I and/or II or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I or II to be formulated, or of combinations thereof with other insectices or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt iof lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substoituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or II or a combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabiliser, antifoams, viscosity regulators, binders, tackifiers as well as fertilisers or other active ingredients in order to obtain special effects.

EXAMPLE 1: PREPARATION

1.1. Intermediates

1.1.1. Pyridyloxyanilines

1.1.1.1.
2-Ethyl-6-methyl-4-(3′,5′-dichloropyrid-2′-yloxy)aniline 23.1 g of 2-ethyl-4-hydroxy-6-methylaniline and 35.7 g of pulverised potassium carbonate are added to 90 ml of dimethyl sulfoxide, and the batch is stirred for 1 hour at room temperature. With constant stirring, a solution of 27.4 g of 2,3,5-trichloropyridine in 30 ml of dimethyl sulfoxide is added dropwise, whereupon the temperature increases to 80°–90° C. The reaction mixture is then stirred for a further 4 hours and subsequently concentrated under a high vacuum, and the residue is taken up in 100 ml of dichloromethane and 100 ml of water. The organic phase is washed with water and dried over sodium sulfate, and the solvent is then distilled off. The residue is recrystallised from hexane, affording the title compound of the formula

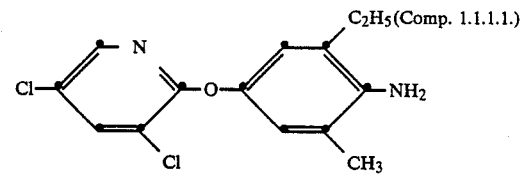

in the form of pale beige-coloured crystals; m.p.: 104°–106° C.

The following compounds are prepared in analogous manner:

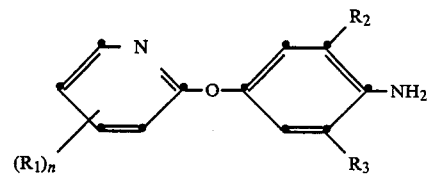

| Comp. | $R_1$ | $R_2$ | $R_3$ | n | m.p. °C. |
|---|---|---|---|---|---|
| 1.1.1.2. | 3-Cl, 5-Cl | $CH_3$ | $CH_3$ | 2 | 118–120 |
| 1.1.1.3. | 3-F, 5-Cl | $CH_3$ | $CH_3$ | 2 | 125–128 |
| 1.1.1.4. | 3-Cl, 5-Cl | $C_2H_5$ | $C_2H_5$ | 2 | 105–106 |
| 1.1.1.5. | 3-Cl, 5-$CF_2CFCl_2$ | $CH_3$ | $CH_3$ | 2 | 139–141 |
| 1.1.1.6. | 3-Cl, 5-$CF_2CFCl_2$ | $CH_3$ | $C_2H_5$ | 2 | 104–107 |
| 1.1.1.7. | 4-Cl, 6-Cl | $CH_3$ | $CH_3$ | 2 | 119–121 |

1.1.2. Pyridyloxyphenylisothiocyanates

1.1.2.1.
2-Ethyl-6-methyl-4-(3′,5′-dichloropyrid-2′-yloxy)-phenylisothiocyanate 7.5 g of thiophosgene, 10 g of calcium carbonate and 80 ml of dichloromethane are stirred in 40 ml of water. A solution of 14.9 g of 2-ethyl-6-methyl-4-(3′,5′-dichloropyrid-2′-yloxy)aniline in 30 ml of dichloroethane is added dropwise at 0°–5° C. to said mixture. The reaction mixture is then stirred for 3 hours at room temperaure and then filtered. The organic phase is isolated from the filtrate, then washed with two 30 ml portions of water, dried over sodium sulfate and, finally, concentrated by evaporation, affording the title compound of the formula

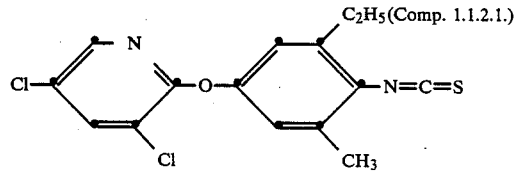

in the form of a yellow oil which crystallises on standing; m.p.: 48°–50° C.

The following compounds are prepared in analogous manner:

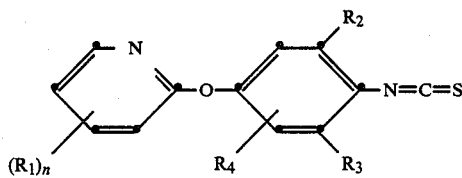

| Comp. | $R_1$ | $R_2$ | $R_3$ | $R_4$ | n | Physical data |
|---|---|---|---|---|---|---|
| 1.1.2.2. | 3-Cl, 5-Cl | $CH_3$ | $CH_3$ | H | 2 | m.p. 89–91° C. |
| 1.1.2.3. | 3-F, 5-Cl | $CH_3$ | $CH_3$ | H | 2 | b.p. 168° C./3 mbar |
| 1.1.2.4. | 3-Cl, 5-Cl | $C_2H_5$ | $C_2H_5$ | H | 2 | b.p. 175° C./2 mbar |
| 1.1.2.5. | 3-Cl, 5-$CF_2CFCl_2$ | $CH_3$ | $CH_3$ | H | 2 | m.p. 79–81° C. |
| 1.1.2.6. | 3-Cl, 5-$CF_2CFCl_2$ | $CH_3$ | $C_2H_5$ | H | 2 | b.p. 170° C./3 mbar |
| 1.1.2.7. | 4-Cl, 6-Cl | $CH_3$ | $CH_3$ | H | 2 | wax |

1.1.3. Pyridyloxyphenylthioureas

1.1.3.1. N-[2-Ethyl-6-methyl-4-(3',5'-dicyhloropyrid-2'-yloxy)-phenyl]-N'-(tert-butyl)thiourea 13.1 g of 2-ethyl-6-methyl-4-(3',5'-dichloropyrid-2'-yloxy)phenylisothiocyanate and 3.7 g of tert-butylamine are taken up in 30 ml of toluene, and the resultant solution is stirred for 3 hours at 45° C. After cooling, the reaction solution is diluted with 50 ml of toluene, washed with water and dried over sodium sulfate. The dry solution is concentrated by evaporation, and the residue is stirred in hexane, affording the title compound of the formula

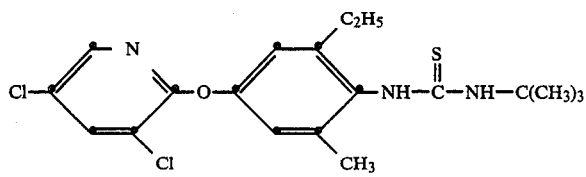

(Comp. 1.1.3.1.)

in the form of a pale beige-coloured powder; m.p.: 96°–98° C.

The following compounds are prepared in analogous manner:

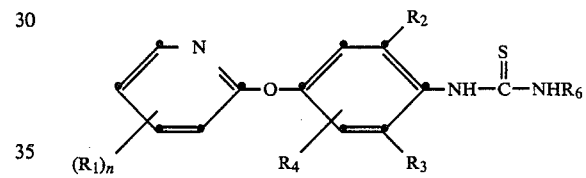

| Comp. | $R_1$ | $R_2$ | $R_3$ | $R_4$ | $R_6$ | n | m.p. °C. |
|---|---|---|---|---|---|---|---|
| 1.1.3.2. | 3-Cl, 5-Cl | $CH_3$ | $CH_3$ | H | $-(CH_2)_3O(CH_2)_3CH_3$ | 2 | 68–70 |
| 1.1.3.3. | 3-Cl, 5-Cl | $CH_3$ | $CH_3$ | H | cyclohexyl | 2 | 146–149 |
| 1.1.3.4. | 3-Cl, 5-Cl | $CH_3$ | $CH_3$ | H | $-C(CH_3)_2-CH_2-C(CH_3)_3$ | 2 | 138–140 |
| 1.1.3.5. | 3-Cl, 5-Cl | $CH_3$ | $CH_3$ | H | $-CH(CH_3)-$cyclohexyl | 2 | 143–145 |
| 1.1.3.6. | 3-Cl, 5-Cl | $CH_3$ | $CH_3$ | H | $-CH_2-CH(CH_3)_2$ | 2 | 104–106 |
| 1.1.3.7. | 3-Cl, 5-Cl | $CH_3$ | $CH_3$ | H | $-C(CH_3)_2-C_2H_5$ | 2 | 118–121 |
| 1.1.3.8. | 3-Cl, 5-Cl | $CH_3$ | $CH_3$ | H | $-CH[\text{cyclopropyl}]_2$ | 2 | 125–127 |
| 1.1.3.9. | 3-Cl, 5-Cl | $CH_3$ | $CH_3$ | H | $-CH_2-$cyclohexyl | 2 | 131–133 |

-continued

| Comp. | R₁ | R₂ | R₃ | R₄ | R₆ | n | m.p. °C. |
|---|---|---|---|---|---|---|---|
| 1.1.3.10. | 3-Cl, 5-Cl | $CH_3$ | $CH_3$ | H | (cyclohexyl with $CH(CH_3)_2$, H) | 2 | 178–180 |
| 1.1.3.11. | 3-Cl, 5-Cl | $CH_3$ | $CH_3$ | H | (cyclohexyl with $CH(CH_3)_2$, H, $CH(CH_3)_2$) | 2 | 174–176 |
| 1.1.3.12. | 3-Cl, 5-Cl | $CH_3$ | $CH_3$ | H | (cyclopentyl with H) | 2 | amorphous |
| 1.1.3.13. | 3-Cl, 5-Cl | $CH_3$ | $CH_3$ | H | $-CH(CH_3)-$ (cyclopropyl) | 2 | 55 |
| 1.1.3.14. | 3-Cl, 5-Cl | $CH_3$ | $CH_3$ | H | $-C(CH_3)_2-$ (cyclohexyl with H) | 2 | 149–151 |
| 1.1.3.15. | 3-Cl, 5-Cl | $CH_3$ | $CH_3$ | H | $-CH(CH_3)_2$ | 2 | 164–166 |
| 1.1.3.16. | 3-Cl, 5-Cl | $C_2H_5$ | $C_2H_5$ | H | $-C(CH_3)_3$ | 2 | 168–169 |
| 1.1.3.17. | 3-F, 5-Cl | $CH_3$ | $CH_3$ | H | $-CH(CH_3)_2$ | 2 | 113–115 |
| 1.1.3.18. | 3-Cl, 5-$CF_2CFCl_2$ | $CH_3$ | $CH_3$ | H | $-C(CH_3)_3$ | 2 | 138–140 |
| 1.1.3.19. | 3-Cl, 5-$CF_2CFCl_2$ | $CH_3$ | $CH_3$ | H | $-CH(CH_3)_2$ | 2 | 160–162 |
| 1.1.3.20. | 3-Cl, 5-$CF_2CFCl_2$ | $CH_3$ | $CH_3$ | H | (bicyclic group) | 2 | 151–153 |
| 1.1.3.21. | 3-Cl, 5-$CF_2CFCl_2$ | $CH_3$ | $CH_3$ | H | $-C(CH_3)_2-C_2H_5$ | 2 | 139–141 |
| 1.1.3.22. | 3-Cl, 5-$CF_2CFCl_2$ | $CH_3$ | $CH_3$ | H | $-C(CH_3)_3$ | 2 | amorphous |
| 1.1.3.23. | 4-Cl, 6-Cl | $CH_3$ | $CH_3$ | H | $-CH(CH_3)_2$ | 2 | 194–196 |
| 1.1.3.24. | 4-Cl, 6-Cl | $CH_3$ | $CH_3$ | H | $-CH(CH(CH_3)_2)_2$ | 2 | 181–183 |
| 1.1.3.25. | 3-Cl, 5-Cl | $CH_3$ | $CH_3$ | H | $-CH(CH_3)-C_2H_5$ | 2 | 138–140 |
| 1.1.3.26. | 3-Cl, 5-Cl | $CH(CH_3)_2$ | $CH(CH_3)_2$ | H | $-C(CH_3)_3$ | 2 | 158–160 |
| 1.1.3.27. | 3-Cl, 5-Cl | $CH(CH_3)_2$ | $CH(CH_3)_2$ | H | $-CH(CH_3)_2$ | 2 | 159–161 |
| 1.1.3.28. | 3-Cl, 5-Cl | $CH(CH_3)_2$ | $CH(CH_3)_2$ | H | $-CH(CH(CH_3)_2)_2$ | 2 | 163–166 |
| 1.1.3.29. | 3-Cl, 5-$CF_3$ | $CH(CH_3)_2$ | $CH(CH_3)_2$ | H | $-C(CH_3)_2$ | 2 | 170–172 |
| 1.1.3.30. | 3-Cl, 5-$CH_3$ | $CH_3$ | $CH_3$ | H | $-CH(CH_3)_2$ | 2 | 130–131 |
| 1.1.3.31. | 3-Cl, 5-Cl | $CH_3$ | $C_2H_5$ | H | $-CH(CH_3)_2$ | 2 | amorphous |
| 1.1.3.32. | 3-Cl, 5-Cl | $C_2H_5$ | $C_2H_5$ | H | $-CH(CH_3)_2$ | 2 | ca. 60 |

1.2. Final products 1.2.1.
N-[2-Ethyl-6-methyl-4-(3′,5′-dichloropyrid-2′-yloxy)-phenyl]-N′-(tert-butyl)-S-methylisothiourea 3.85 g of N-[2-ethyl-6-methyl-4-(3′,5′-dichloropyrid-2′-yloxy)phenyl]-N′-(tert-butyl)thiourea are added to 40 ml of ethanol. After the addition of 1.7 g of methyl iodide, the batch is stirred for 3 hours under slight reflux. The reaction solution is subsequently concentrated by evaporation, and the residue is taken up in dichloromethane and 10% sodium carbonate solution. The organic phase is then washed with water, dried over sodium sulfate and evaporated to dryness, affording the title compound of the formula

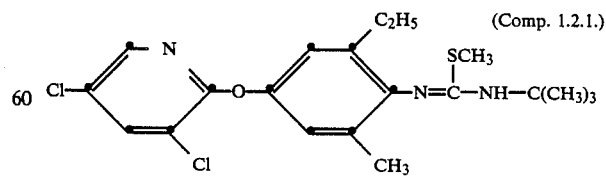

(Comp. 1.2.1.)

in the form of a pale yellow oil; refractive index $n_D^{49}$: 1.5610.

The following compounds are prepared in analogous manner:

solution is stirred for 3 hours at room temperature, and the resultant precipitate is then isolated by suction filtration and dried, affording the title compound of the formula

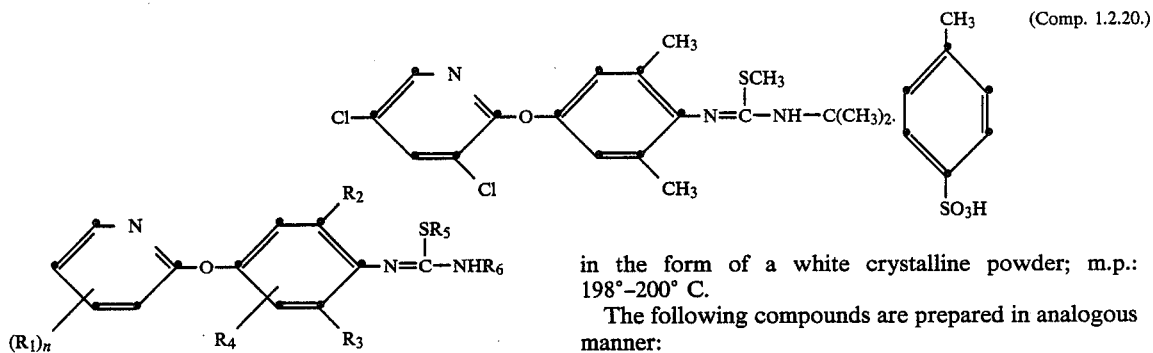
(Comp. 1.2.20.)

in the form of a white crystalline powder; m.p.: 198°-200° C.

The following compounds are prepared in analogous manner:

| Comp. | R₁ | R₂ | R₃ | R₄ | R₅ | R₆ | n | Physical data |
|---|---|---|---|---|---|---|---|---|
| 1.2.2 | 3-Cl, 5-Cl | CH₃ | CH₃ | H | CH₃ | —CH(CH₃)—⟨cyclohexyl-H⟩ | 2 | $n_D^{49}$ 1.5840 |
| 1.2.3 | 3-Cl, 5-Cl | CH₃ | CH₃ | H | CH₃ | —CH₂—CH(CH₃)₂ | 2 | |
| 1.2.4 | 3-Cl, 5-Cl | CH₃ | CH₃ | H | CH₃ | —C(CH₃)₂—C₂H₅ | 2 | $n_D^{49}$ 1.5820 |
| 1.2.5 | 3-Cl, 5-Cl | CH₃ | CH₃ | H | CH₃ | —CH[cyclopropyl]₂ | 2 | m.p. 88–90° C. |
| 1.2.6 | 3-Cl, 5-Cl | CH₃ | CH₃ | H | CH₃ | —⟨cyclopentyl-H⟩ | 2 | $n_D^{49}$ 1.5980 |
| 1.2.7 | 3-Cl, 5-Cl | CH₃ | CH₃ | H | CH₃ | —CH(CH₃)—⟨cyclopropyl⟩ | 2 | $n_D^{49}$ 1.5900 |
| 1.2.8 | 3-Cl, 5-Cl | C₂H₅ | C₂H₅ | H | CH₃ | —C(CH₃)₃ | 2 | $n_D^{49}$ 1.5774 |
| 1.2.9 | 3-Cl, 5-CF₂CFCl₂ | CH₃ | CH₃ | H | CH₃ | —C(CH₃)₃ | 2 | $n_D^{49}$ 1.5505 |
| 1.2.10 | 3-Cl, 5-CF₂CFCl₂ | CH₃ | CH₃ | H | CH₃ | —CH(CH₃)₂ | 2 | $n_D^{49}$ 1.5560 |
| 1.2.11 | 3-Cl, 5-Cl | CH(CH₃)₂ | CH(CH₃)₂ | H | CH₃ | —C(CH₃)₃ | 2 | amorphous |
| 1.2.12 | 3-Cl, 5-Cl | CH(CH₃)₂ | CH(CH₃)₂ | H | CH₃ | —CH(CH(CH₃)₂)₂ | 2 | m.p. 109°–110° C. |
| 1.2.13 | 3-Cl, 5-CF₃ | CH(CH₃)₂ | CH(CH₃)₂ | H | n-C₄H₉ | —C(CH₃)₃ | 2 | $n_D^{40}$ 1.5239 |
| 1.2.14 | 3-Cl, 5-CH₃ | CH₃ | CH₃ | H | CH₃ | —CH(CH₃)₂ | 2 | m.p. 111–113° C. |
| 1.2.15 | 3-Cl, 5-Cl | CH₃ | C₂H₅ | H | CH₃ | —CH(CH₃)₂ | 2 | $n_D^{24}$ 1.5959 |
| 1.2.16 | 3-Cl, 5-Cl | C₂H₅ | C₂H₅ | H | CH₃ | —CH(CH₃)₂ | 2 | $n_D^{24}$ 1.5880 |
| 1.2.17 | 3-Cl, 5-Cl | CH₃ | CH₃ | H | CH₃ | —CH(CH₃)₂ | 2 | resin |
| 1.2.18 | 3-Cl, 5-Cl | CH₃ | CH₃ | H | n-C₆H₁₃ | —CH(CH₃)₂ | 2 | resin |
| 1.2.19 | 3-Cl, 5-Cl | CH₃ | CH₃ | H | CH₃ | —CH₂CF₃ | 2 | 102–103° C. |

1.2.20. The 4-toluenesulfonic acid salt of N-[2,6-dimethyl-4-(3',5'-dichloropyrid-2'-yloxy)-phenyl]-N'-isopropyl-S-methylisothiourea 5.0 g of N-[2,6-dimethyl-4-(3',5'-dichloropyrid-2'-yloxy)phenyl]-N'-isopropyl-S-methylisothiourea are dissolved in 20 ml of absolute diethyl ether, followed by the dropwise addition of a solution of 2.2 g of 4-toluenesulfonic acid in 10 ml of diethyl ether. The reaction

| Comp. | $R_1$ | $R_2$ | $R_3$ | $R_4$ | $R_5$ | $R_6$ | n | Y | m.p. °C. |
|---|---|---|---|---|---|---|---|---|---|
| 1.2.21 | 3-Cl, 5-Cl | $CH_3$ | $CH_3$ | H | $CH_3$ | $-CH(CH_3)_2$ | 2 | $(COOH)_2$ | 175 decomp. |
| 1.2.22 | 3-Cl, 5-Cl | $CH_3$ | $CH_3$ | H | $CH_3$ | $-CH(CH_3)_2$ | 2 | HI | >250 |

The HI salts can also be obtained direct in process 1.2.1. if after the addition of methyl iodide the precipitate is isolated and purified as described above.

EXAMPLE 2

Formulation Examples for active ingredients of formulae I and II according to Preparatory Examples 1.1.3 and 1.2. (throughout, percentages are by weight)

| 2.1. Emulsifiable concentrates | (a) | (b) |
|---|---|---|
| a compound or compounds according to Preparatory Examples 1.1.3 and/or 1.2 | 10% | 25% |
| calcium dodecylbenzenesulfonate | — | 5% |
| castor oil polyethylene glycol ether (36 moles of ethylene oxide) | 25% | 5% |
| tributylphenol polyethylene glycol ether (30 moles of ethylene oxide) | — | — |
| cyclohexanone | — | 40% |
| butanol | 15% | — |
| xylene mixture | — | 25% |
| ethyl acetate | 50% | — |

Emulsions of any required concentration can be produced from such concentrates by dilution with water.

| 2.2. Solutions | (a) | (b) |
|---|---|---|
| a compound or compounds according to Preparatory Examples 1.1.3 and/or 1.2 | 10% | 5% |
| polyethylene glycol 400 | 70% | — |
| N—methyl-2-pyrrolidone | 20% | 20% |
| epoxidised coconut oil | — | 1% |
| petroleum distillate (boiling range 160-190° C.) | — | 74% |

These solutions are suitable for application in the form of microdrops.

| 2.3. Granulates | (a) | (b) |
|---|---|---|
| a compound or compounds according to Preparatory Examples 1.1.3 and/or 1.2 | 5% | 10% |
| kaolin | 94% | — |
| highly dispersed silicic acid | 1% | — |
| attapulgite | — | 90% |

The active ingredient or ingredients is or are dissolved in methylene chloride, the solution is sprayed onto the carrier, and the solvent is subsequently evaporated off in vacuo.

| 2.4. Extruder granulate | |
|---|---|
| a compound or compounds according to Preparatory Examples 1.1.3 and/or 1.2 | 10% |
| sodium lignosulfonate | 2% |
| carboxymethylcellulose | 1% |
| kaolin | 87% |

The active ingredient or ingredients is or are mixed and ground with the adjuvants, and the mixture is subsequently moistened with water. The mixture is extruded and then dried in a stream of air.

| 2.5. Coated granulate | |
|---|---|
| a compound or compounds according to Preparatory Examples 1.1.3. and/or 1.2 | 3% |
| polyethylene glycol 200 | 3% |
| kaolin | 94% |

The finely ground active ingredient or ingredients is or are uniformly applied, in a mixer, to the kaolin moistened with polyethlene glycol. Non-dusty coated granulates are obtained in this manner.

| 2.6. Dusts | (a) | (b) | (c) | (d) |
|---|---|---|---|---|
| a compound or compounds according to Preparatory Examples 1.1.3 and/or 1.2 | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient or ingredients and, optionally, grinding the mixture in a suitable mill.

| 2.7. Wettable powders | (a) | (b) | (c) |
|---|---|---|---|
| a compound or compounds according to Preparatory Examples 1.1.3 and/or 1.2 | 20% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 67% | 27% | — |

The active ingredient or ingredients is or are thoroughly mixed with the adjuvants and the mixture is thoroughly ground in a suitable mill, affording wettable powders which can be diluted with water to give suspensions of the desired concentration.

| 2.8. Suspension concentrate | |
|---|---|
| a compound or compounds according to Preparatory Examples 1.1.3 and/or 1.2 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or ingredients is or are intimately mixed with the adjuvants, giving a suspension concentrate from which suspensions of any desired concentration can be obtained by dilution with water.

EXAMPLE 3: BIOLOGICAL TESTS

3.1. Action against *Musca domestica*

50 g of freshly prepared CSMA nutrient substrate for maggots are charged into a beaker. 5 ml of an acetonic solution containing 1% by weight of the test compound is pipetted onto the nutrient substrate present in the beaker. The substrate is then thoroughly mixed and the acetone subsequently allowed to evaporate over a period of at least 20 hours.

Then 25 one-day-old maggots of *Musca domestica* are put into the beaker containing the treated nutrient substrate. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

Compounds according to Examples 1.1.3 and 1.2 exhibit good activity in this test.

3.2. Action against *Lucilia sericata*

1 ml of an aqueous formulation containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

In this test, compounds according to Examples 1.1.3 and 1.2 exhibit good activity against *Lucilia sericata*.

3.3. Action against *Aedes aegypti*

A concentration of 12.5 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker containing the test compound. Mortality counts are made after 2 and 7 days.

Compounds according to Examples 1.1.3 and 1.2 exhibit good activity in this test.

3.4. Insecticidal Action Against Feeding Insects

Cotton plants (about 20 cm high) are sprayed with an aqueous emulsion (obtained from a 10% emulsifiable concentrate) containing 100 ppm of the test compound. After the spray coating has dried, the cotton plants are populated with *Spodoptera littoralis* and *Heliothis virescens* larvae in the $L_3$-stage. The test is carried out at 24° C. and 60% relative humidity. At 24 hour intervals, a mortality count is made and the larvae are also examined for inhibition of development and moulting.

Compounds according to Examples 1.1.3 and 1.2 exhibit good activity in this test.

3.5. Action Against *Spodoptera littoralis* and *Heliothis virescens* (Larvae and Eggs):

Three cotton plants each having a height of about 15–20 cm and grown in pots are treated with a sprayable liquid preparation of the test compound. After the spray coating was dried, the potted plants are placed in a metal container having a capacity of about 20 liters and covered with a glass plate. The humidity in the interior of the covered container is regulated such that no water of condensation forms. Direct light falling on the plants is avoided. The three plants are then infested altogether with:

(a) 50 larvae of *Spodoptera littoralis* or *Heliothis virescens* in the $L_1$-stage;
(b) 20 larvae of *Spodoptera littoralis* or *Heliothis virescens* in the $L_3$-stage;
(c) 2 egg deposits of *Spodoptera littoralis* or *Heliothis virescens*. (The procedure is that two leaves of each plant are put into a plexiglass cylinder sealed at both ends with gauze. Two egg deposits of Spodoptera, or a part of a cotton leaf with eggs of Heliothis deposited thereon, are added to the leaves sealed in the cylinder).

Evaluation in comparison with untreated controls is made after 4 to 5 days, taking into account the following criteria:

(a) the number of still living larvae,
(b) inhibition of larval development and moulting,
(c) feeding damage (shredding and perforation damage),
(d) hatching rate (number of larvae hatched from the eggs).

In this test, compounds according to Examples 1.1.3 and 1.2 exhibit good overall activity at a concentration of 400 ppm.

3.6. Ovicidal Action Against *Spodoptera littoralis*

Eggs of *Spodoptera littoralis* deposited on filter paper are cut out of the paper and immersed in a 0.05% by weight solution of the test compound in a 1:1 mixture of acetone-water. The treated deposits are then removed from this mixture and kept in plastic dishes at 28° C. and 60% relative humidity. The hatching rate, i.e. the number of larvae which have developed from the treated eggs, is determined after 5 days.

Compounds according to Examples 1.1.3 and 1.2 show good activity in this test.

3.7. Action Against *Laspeyresia pomonella* (Eggs)

Egg deposits of *Laspeyresia pomonella* not more than 24 hours old are immersed on filter paper for 1 minute in an aqueous acetonic solution containing 400 ppm of the test compound.

After the solution has dried, the filter paper and the eggs are placed in petri dishes and kept at a temperature of 28° C. The percentage of larvae hatched from the treated eggs is evaluated after 6 days.

Compounds according to Examples 1.1.3 and 1.2 exhibit good activity in this test.

3.8. Influence on the Reproduction of *Anthonomus grandis*

*Anthonomus grandis* adults which are not more than 24 hours old after hatching are transferred in groups of 25 to barred cages. The cages are then immersed for 5 to 10 seconds in an acetonic solution containing 0.1% by weight of the test compound. After the beetles have dried, they are placed in covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. A count is made after 7 days to determine whether larvae have developed from the eggs.

The duration of the reproduction inhibiting effect of the test compounds is determined by monitoring the egg deposits of the beetles over a period of about 4 weeks. Evaluation is made by assessing the reduction in the number of deposited eggs and hatched larvae in comparison with untreated controls.

Compounds according to Examples 1.1.3 and 1.2 exhibit a good reproduction inhibiting effect in this test.

3.9. Action Against *Anthonomus grandis* (Adults)

Two cotton plants in the 6-leaf stage, in pots, are each sprayed with a wettable aqueous emulsion formulation containing 100 ppm of the test compound. After the spray coating has dried (about 1½ hours), each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the antifeeding action as compared with untreated controls.

Compounds according to Examples 1.1.3 and 1.2 exhibit good activity in this test.

3.10. Action Against *Epilachna varivestis*

*Phaseolus vulgaris* plants (dwarf beans) about 15–20 cm in height are sprayed with aqueous emulsion formulations of the test compound in a concentration of 800 ppm. After the spray coating has dried, each plant is populated with 5 larvae of *Epilachna varivestis* (Mexican bean beetle) in the L4-stage. A plastic cylinder is slipped over the treated plants and covered with a copper gauze top. The test is carried out at 28° C. and 60% relative humidity. The percentage mortality is determined after 2 and 3 days. Evaluation of feeding damage (anti-feeding effect), and of inhibition of development and shedding, is made by observing the test insects for a further 3 days.

Compounds according to Examples 1.1.3 and 1.2 exhibit good activity in this test. 3.11: Ovicidal Action Against *Heliothis virescens* and *Spodoptera littoralis*

Corresponding amounts of a wettable powder formulation containing 25% by weight of the test compound are mixed with sufficient water to produce an aqueous emulsion with an active ingredient concentration of 400 ppm. One-day-old egg deposits of Heliothis on cellophane and of Spodoptera on paper are immersed in these emulsions for 3 minutes and then collected by suction on round filters. The treated deposits are placed in petri dishes and kept in the dark at 28° C. and 60% relative humidity. The hatching rate, i.e. the number of larvae which have developed from the treated eggs, in comparison with untreated controls, is determined after 5 to 8 days.

In this test, compounds according to Examples 1.1.3 and 1.2 exhibit an 80 to 100% ovicidal activity (mortality) against *Heliothis virescens* and *Spodoptera littoralis*.

3.12. Action Against Plant-Destructive Acarids:
*Tetranychus urticae* (OP-Sensitive) and *Tetranychus cinnabarinus* (OP-Tolerant)

16 hours before the test for acaricidal action, the primary leaves of *Phaseolus vulgaris* plants are infected with an infested piece of leaf from a mass culture of *Tetranychus urticae* (OP-sensitive) or *Tetranychus cinnabarinus* (OP-tolerant). (The tolerance refers to diazinone). The treated infested plants are sprayed to drip point with a test solution containing the respective test compound in concentrations of 0.75 to 400 ppm. A count of the number of living and dead imagines and larvae (all mobile stages) is made under a stereoscopic microscope after 24 hours and again after 7 days. One plant is used for each test compound at its given concentration and for each test species. During the test run, the plants are kept in greenhouse compartments at 25° C.

In this test, compounds according to Examples 1.1.3 and 1.2 exhibit good activity against *Tetranychus urticae* and *Tetranychus cinnabarinus*.

What is claimed is:

1. A compound of formula I

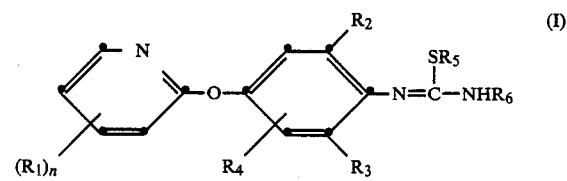

wherein
the substituents $R_1$ are each independently halogen, $C_1$–$C_3$alkyl or $C_1$–$C_3$alkyl substituted by 1–7 halogens, or —COOR$_7$;
$R_2$, $R_3$ and $R_7$ are each independently $C_1$–$C_5$alkyl, with the proviso that $R_2$ and $R_3$ are not simultaneously methyl if $R_6$ is tert-butyl and the substituents $R_1$ are chlorine and/or trifluoromethyl;
$R_4$ is hydrogen or methyl;
$R_5$ is $C_1$–$C_6$alkyl;
$R_6$ is $C_1$–$C_{12}$alkyl or $C_1$–$C_{12}$alkyl substituted by $C_1$–$C_6$alkoxy or by 1 to 9 atoms selected from fluorine, chlorine, and bromine;
$C_3$–$C_8$cycloalkyl or $C_3$–$C_8$cycloalkyl substituted by one or two $C_1$–$C_3$alkyl groups, $C_3$–$C_8$cycloalkyl-$C_1$–$C_4$-alkyl,
or a $C_7$–$C_{10}$bicyclic alkyl radical; and
n is 0 to 4;
or an agriculturally acceptable salt thereof with an organic or inorganic acid.

2. A compound of formula I according to claim 1, wherein
the substituents $R_1$ are each independently fluorine, chlorine or a mono- or polyhalogenated $C_1$–$C_3$alkyl group;
$R_2$ and $R_3$ are each independently $C_1$–$C_3$alkyl, with the proviso that $R_2$ and $R_3$ are not imultaneously methyl if $R_6$ is tert-butyl and the substituents $R_1$ are chlorine and/or trifluoromethyl;
$R_4$ is hydrogen;
$R_5$ is $C_1$–$C_3$alkyl;
$R_6$ is $C_1$–$C_8$alkyl, $C_1$–$C_4$alkoxy-$C_1$–$C_4$alkyl, $C_3$–$C_6$-cycloalkyl, $C_3$–$C_6$cycloalkyl substituted by one or two $C_1$–$C_3$alkyl groups, or $C_3$–$C_6$cycloalkyl-$C_1$–$C_3$alkyl; and
n is 1 or 2.

3. A compound of formula I according to claim 2, wherein the substituents $R_1$ are each independently chlorine or $CF_2CFCl_2$; $R_2$ and $R_3$ are each independently methyl or ethyl, with the proviso that $R_2$ and $R_3$ are not simultaneously methyl if $R_6$ is tert-butyl and the substituents $R_1$ are chlorine and/or trifluoromethyl; $R_4$ is hydrogen; $R_5$ is methyl; $R_6$ is $C_1$–$C_5$alkyl or $C_3$–$C_6$cycloalkyl; and n is 2.

4. The compound according to claim 3 of the formula

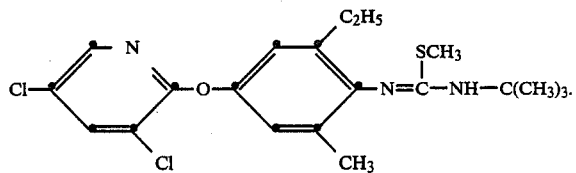
5. The compound according to claim 2 of the formula
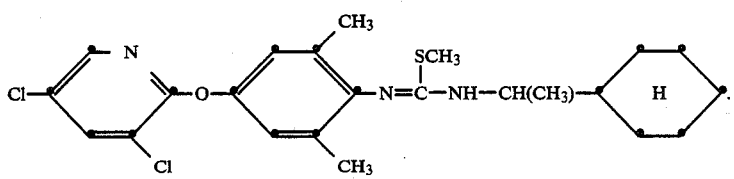
6. The compound according to claim 3 of the formula
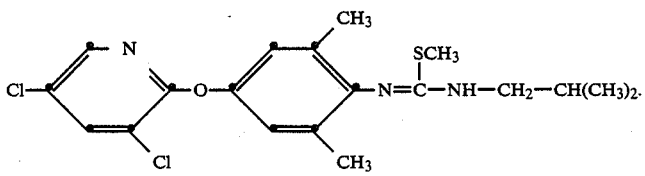
7. The compound according to claim 3 of the formula
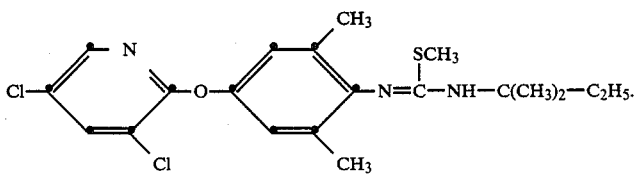
8. The compound according to claim 2 of the formula
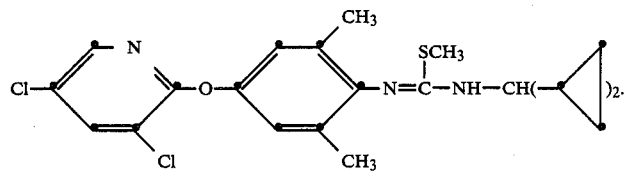
9. The compound according to claim 3 of the formula
10. The compound according to claim 2 of the formula
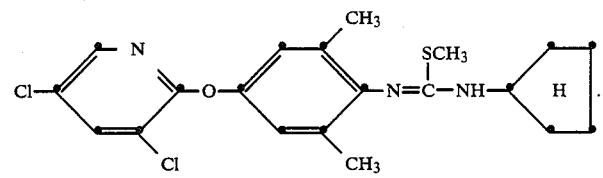

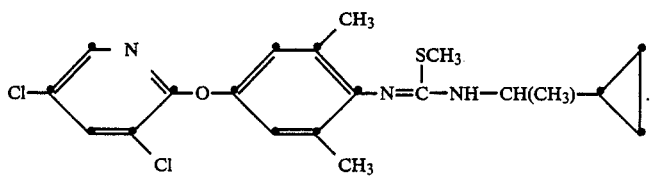

11. The compound according to claim 3 of the formula

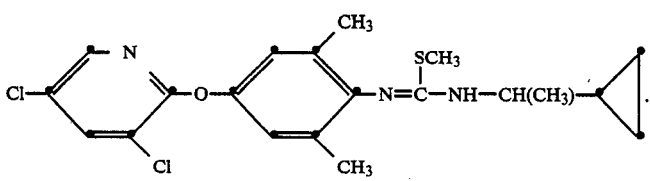

12. The compound according to claim 3 of the formula

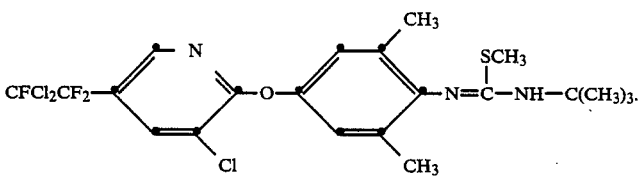

13. The compound according to claim 3 of the formula

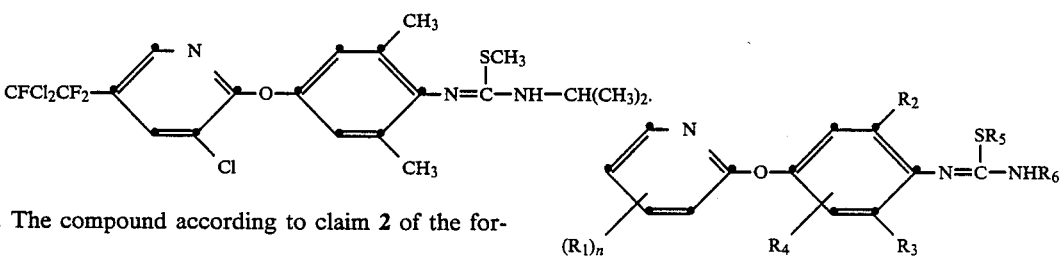

14. The compound according to claim 2 of the formula

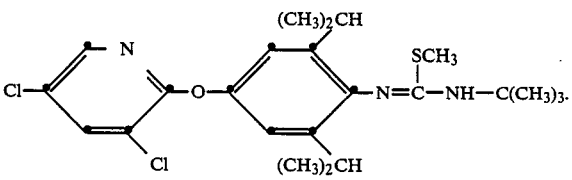

15. The compound according to claim 2 of the formula

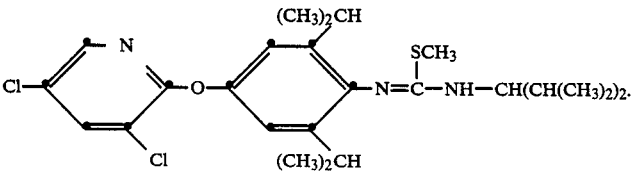

16. A pesticidal composition which comprises, as active ingredient, a pesticidally effective amount of a compound of formula I (I)

or an agriculturally acceptable salt thereof with an organic or inorganic acid, in which formula
the substituents $R_1$ are each independently halogen, $C_1$–$C_3$alkyl or $C_1$–$C_3$alkyl substituted by 1–7 halogen, or —$COOR_7$;

$R_2$, $R_3$ and $R_7$ are each independently $C_1$–$C_5$alkyl, with the proviso that $R_2$ and $R_3$ are not simultaneously methyl if $R_6$ is tert-butyl and the substituents $R_1$ are chlorine and/or trifluoromethyl;

$R_4$ is hydrogen or methyl;

$R_5$ is $C_1$–$C_6$alkyl;

$R_6$ is $C_1$–$C_{12}$alkyl or $C_1$–$C_{12}$alkyl substituted by $C_1$–$C_6$alkoxy or by 1 to 9 atoms selected from fluorine chlorine and bromine; $C_3$–$C_8$cycloalkyl or $C_3$–$C_8$cycloalkyl substituted by one or two $C_1$–$C_3$alkyl groups, $C_3$–$C_8$cycloalkyl-$C_1$–$C_4$-alkyl, or a $C_7$–$C_{10}$bicyclic alkyl radical; and n is 0 to 4;

together with a conventional carrier or other adjuvant.

17. A pesticidal composition according to claim 16, which comprises, as active ingredient, a compound of formula I, wherein the substituents $R_1$ are each independently fluorine, chlorine or a $C_1$–$C_3$alkyl group substituted by 1 to 7 halogens;

$R_2$ and $R_3$ are each independently $C_1$–$C_3$alkyl, with the proviso that $R_2$ and $R_3$ are not simultaneously methyl if $R_6$ is tert-butyl and the substituents $R_1$ are chlorine and/or trifluoromethyl;

$R_4$ is hydrogen;

$R_5$ is $C_1$–$C_3$alkyl;

$R_6$ is $C_1$–$C_8$alkyl, $C_1$–$C_4$alkoxy-$C_1$–$C_4$alkyl, $C_3$–$C_6$-cycloalkyl, $C_3$–$C_6$cycloalkyl substituted by one or two $C_1$–$C_3$alkyl groups, or $C_3$–$C_6$cycloalkyl-$C_1$–$C_3$alkyl; and n is 1 or 2.

18. A pesticidal composition according to claim 17, which comprises, as active ingredient, a compound of formula I, wherein the substituents $R_1$ are each independently chlorine or $CF_2CFCl_2$; $R_2$ and $R_3$ are each independently methyl or ethyl, with the proviso that $R_2$ and $R_3$ are not simultaneously methyl if $R_6$ is tert-butyl and the substituents $R_1$ are chlorine and/or trifluoromethyl; $R_4$ is hydrogen; $R_5$ is methyl; $R_6$ is $C_1$–$C_5$alkyl or $C_3$–$C_6$-cycloalkyl; and n is 2.

19. A method of controlling pests of animals and plants selected from insects and arachnids, which method comprises applying to said pests or their locus a pesticidally effective amount of a compound of formula I

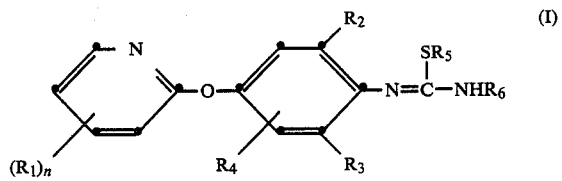

wherein the substituents $R_1$ are each independently halogen, $C_1$–$C_3$alkyl or $C_1$–$C_3$alkyl substituted by 1 ∝ 7 halogens, or —$COOR_7$;

$R_2$, $R_3$ and $R_7$ are each independently $C_1$–$C_5$alkyl, with the proviso that $R_2$ and $R_3$ are not simultaneously methyl if $R_6$ is tert-butyl and the substituents $R_1$ are chlorine and/or trifluoromethyl;

$R_4$ is hydrogen or methyl;

$R_5$ is $C_1$–$C_6$alkyl;

$R_6$ is $C_1$–$C_{12}$alkyl or $C_1$–$C_{12}$alkyl substituted by $C_1$–$C_6$alkoxy or by 1 to 9 atoms selected from fluorine, chlorine and bromine; or $C_3$–$C_8$cycloalkyl or $C_3$–$C_8$cycloalkyl substituted by one or two $C_1$–$C_3$alkyl groups, $C_3$–$C_8$cycloalkyl-$C_1$–$C_4$-alkyl, $C_7$–$C_{10}$bicyclic alkyl radical; and n is 0 to 4;

or an agriculturally acceptable salt thereof with an organic or inorganic acid.

* * * * *